(12) United States Patent
Hüglin et al.

(10) Patent No.: US 6,221,342 B1
(45) Date of Patent: Apr. 24, 2001

(54) COSMETIC USE OF BIS(RESORCINYL) TRIAZINE DERIVATIVES

(75) Inventors: Dietmar Hüglin, Eimeldingen; Helmut Luther, Grenzach-Wyhlen; Dieter Reinehr, Kandern, all of (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/485,948

(22) PCT Filed: Aug. 8, 1998

(86) PCT No.: PCT/EP98/05042

§ 371 Date: Feb. 17, 2000

§ 102(e) Date: Feb. 17, 2000

(87) PCT Pub. No.: WO99/08653

PCT Pub. Date: Feb. 25, 1999

(30) Foreign Application Priority Data

Aug. 20, 1997 (EP) .................................. 97810585

(51) Int. Cl.⁷ .............. A61K 7/42; A61K 7/44; A61K 7/00; A61K 31/53
(52) U.S. Cl. .............. 424/59; 424/60; 424/400; 424/401; 514/241
(58) Field of Search ............... 424/59, 60, 400, 424/401; 514/241

(56) References Cited

FOREIGN PATENT DOCUMENTS

| 639329 | 4/1964 | (BE) |
| 650932 | 1/1965 | (BE) |
| 480090 | 10/1969 | (CH) |
| 0775698 | 5/1997 | (EP) |
| 878469 | 11/1998 | (EP) |
| 95/22959 | 8/1995 | (WO) |

*Primary Examiner*—Shelley A. Dodson
(74) *Attorney, Agent, or Firm*—Kevin T. Mansfield

(57) ABSTRACT

A description is given of the use of bis(resorcinyl)triazines of formula (1) wherein $R_1$ and $R_2$ are each independently of the other hydrogen; $C_1$–$C_{18}$alkyl; $C_2$–$C_{18}$alkenyl; a radical of formula —$CH_2$—CH(—OH)—$CH_2$—O—$T_1$; a radical of formula (1a); or a radical of radical of formula (1b); $R_3$ and $R_4$ are each independently of the other hydrogen or $C_1$–$C_5$alkyl; $R_5$ is hydroxy; $C_1$–$C_5$alkoxy which is unsubstituted or substituted by one or several OH groups; amino; mono- or di-$C_1$–$C_5$alkylamino; M; a radical of formula (1c); (1d); (1e); (1f); (1g); or (1h); $R_6$ is a direct bond; a straight-chain or branched $C_1$–$C_4$alkylene radical or a radical of formula (a) or (b); $R_7$, $R_8$ and $R_9$ are each independently of one another $C_1$–$C_{18}$alkyl; $C_1$–$C_{18}$alkoxy or a radical of formula (1i), $R_{10}$, $R_{11}$ and $R_{12}$ are each independently of one another $C_1$–$C_{14}$alkyl which is unsubstituted or substitued by one or several OH groups; $R_{13}$ is hydrogen; M; $C_1$–$C_5$alkyl; or a radical of formula (c) $R_{14}$ is $C_1$–$C_5$alkyl; M is a metal cation; $T_1$ is hydrogen; or $C_1$–$C_8$alkyl; $m_1$ is 1 to 3; $m_2$ is 2 to 14; and $p_1$ is 0; or a number from 1 to 5, for protecting human and animal skin and hair from the damaging effect of UV radiation. The compounds used according to this invention are very powerful UVA absorbers with fractions in the UVB range and are particularly suitable as sunscreens in cosmetic, pharmaceutical and veterinary compositions.

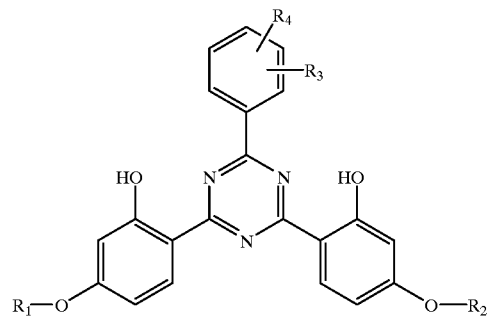

(1)

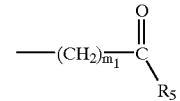

(1a)

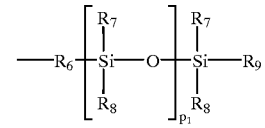

(1b)

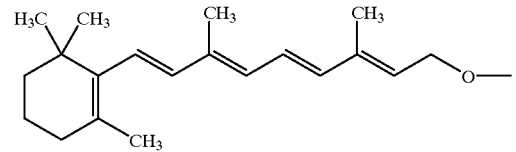

(1c)

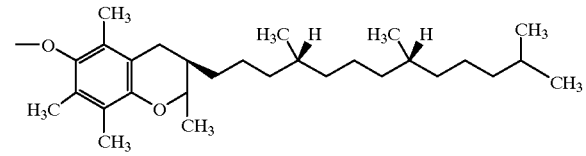

(1d)

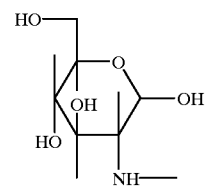

(1e)

-continued
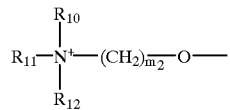 (1f)
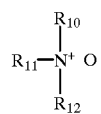 (1g)
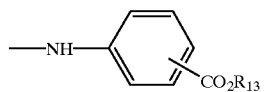 (1h)
-continued
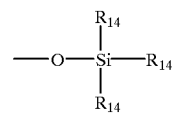 (1i)
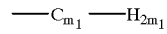 (a)
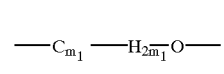 (b)
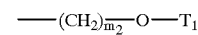 (c)
12 Claims, No Drawings

COSMETIC USE OF BIS(RESORCINYL) TRIAZINE DERIVATIVES

The present invention relates to the use of selected bis(resorcinyl)triazine derivatives for protecting human and animal skin and hair from the damaging effect of UV radiation and to a cosmetic formulation comprising these bis(resorcinyl)triazine derivatives.

The bis(resorcinyl)triazines used according to this invention correspond to formula (1)

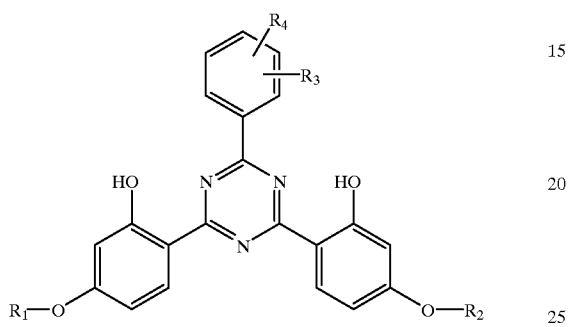

wherein $R_1$ and $R_2$ are each independently of the other hydrogen; branched $C_5$–$C_{18}$alkyl; $C_2$–$C_{18}$alkenyl; a radical of formula —$CH_2$—CH(—OH)—$CH_2$—O—$T_1$; a radical of formula (1a)

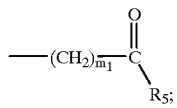

or a radical of formula (1b)

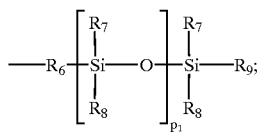

$R_3$ and $R_4$ are each independently of the other hydrogen or $C_1$–$C_5$alkyl;

$R_5$ is hydroxy; $C_1$–$C_5$alkoxy which is unsubstituted or substituted by one or several OH groups; amino; mono or di-$C_1$–$C_5$alkylamino; M; a radical of formula (1c)

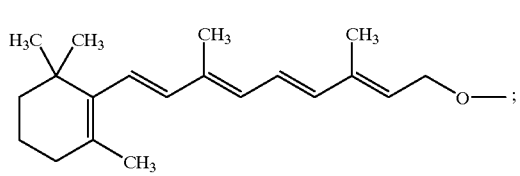

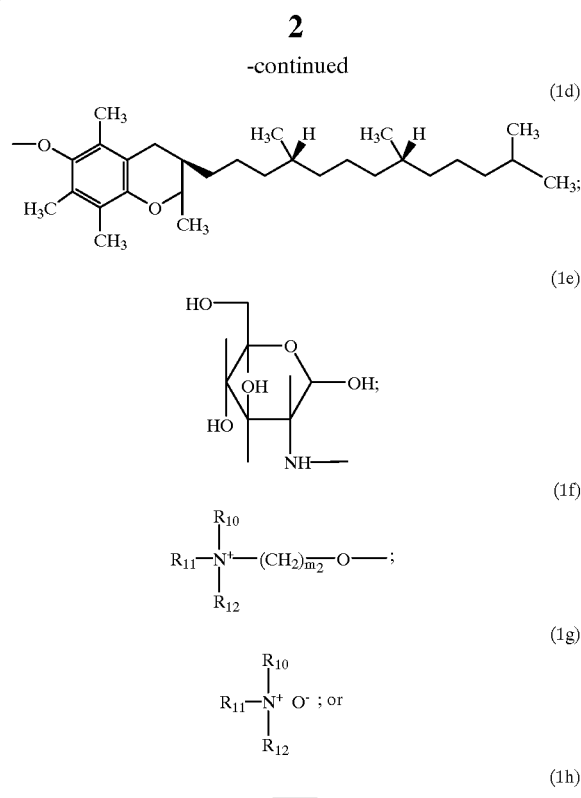

$R_6$ is a direct bond; a straight-chain or branched $C_1$–$C_4$alkylene radical or a radical of formula

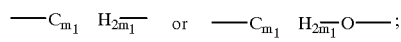

$R_7$, $R_8$ and $R_9$ are each independently of one another $C_1$–$C_{18}$alkyl; $C_1$–$C_{18}$alkoxy or a radical of formula (1i)

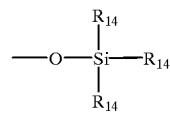

$R_{10}$, $R_{11}$ and $R_{12}$ are each independently of one another $C_1$–$C_{14}$alkyl which is unsubsttuted or substituted by one or several OH groups;
$R_{13}$ is hydrogen; M; $C_1$–$C_5$alkyl; or a radical of formula —$(CH_2)_{m_2}$—O—$T_1$;
$R_{14}$ is $C_1$–$C_5$alkyl;
M is a metal cation;
$T_1$ is hydrogen; or $C_1$–$C_8$alkyl;
$m_1$ is 1 to 3;
$m_2$ is 2 to 14; and
$p_1$ is 0; or a number from 1 to 5.
$C_1$–$C_5$Alkyl, $C_1$–$C_8$alkyl and $C_1$–$C_{18}$alkyl are straight-chain or branched allcyl radicals, such as methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl or octadecyl.

$C_1$–$C_5$Alkoxy and $C_1$–$C_{18}$alkoxy are straight-chain or branched alkoxy radicals, such as methoxy, ethoxy, n-propoxy, isopropoxy, n-butyloxy, sec-butyloxy, tert-butyloxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy or octadecyloxy.

$C_2$–$C_{18}$Alkenyl is, for example, allyl, methallyl, isopropenyl, 2-butenyl, 3-butenyl, isobutenyl, n-penta-2,4-dienyl, 3-methylbut-2-enyl, n-oct-2-enyl, n-dodec-2-enyl, iso-dodecenyl, n-dodec-2-enyl or n-octadec-4-enyl.

Examples of mono- or di-$C_1$–$C_5$alkylamino are methylamino, ethylamino, propylamino, n-butylamino, sec-butylamino, tert-butylamino, pentylamino, dimethylamino, diethylamino; dipropylamino; dibutylamino or methylethylamino.

Examples of metal cations are the lithium, potassium, sodium, calcium, magnesium, copper or zinc ion.

According to this invention, it is preferred to use bis(resorcinyl) compounds of formula (2)

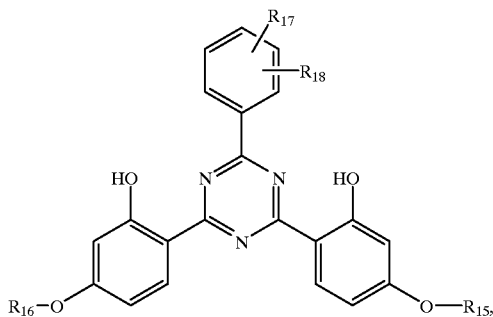

wherein $R_{15}$ and $R_{16}$ are each independently of the other branched $C_5$–$C_{18}$alkyl; or

—$CH_2$—$CH(—OH)$—$CH_2$—O—$T_1$;

$R_{17}$ and $R_{18}$ are each independently of the other hydrogen or $C_1$–$C_5$alkyl; and $T_1$ is hydrogen; or $C_1$–$C_5$alkyl.

Preeminently interesting compounds are those of formula (2), wherein

R15 and $R_{16}$ are each independently of the other branched $C_5$–$C_{18}$alkyl or —$CH_2$—$CH(—OH)$—$CH_2$—O—$T_1$;

$R_{17}$ and $R_{18}$ are hydrogen; and $T_1$ is hydrogen; or $C_1$–$C_5$alkyl; and in particular those compounds of formula (2), wherein $R_{15}$ and $R_{16}$ are each independently of the other branched $C_{5-18}$alkyl; and $R_{17}$ and $R_{18}$ are hydrogen.

Very particularly preferred are those triazine compounds of formula (2), wherein $R_{15}$ and $R_{16}$ have the same meaning.

Other triazine derivatives which may be used according to this invention are those corresponding to formula (3)

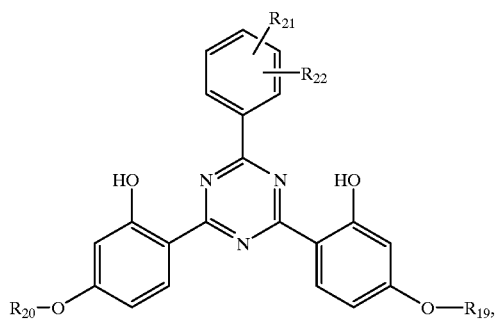

wherein $R_{19}$ and $R_{20}$ are each independently of the other the radical of formula

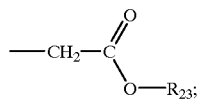

and $R_{21}$, $R_{22}$ $R_{23}$ are each independently of one another hydrogen; or $C_1$–$C_{10}$alkyl.

Examples to be mentioned of compounds of formula (1) are:

2-(4'-methylphenyl)4,6-bis(2'-hydroxy-4'-n-octyloxyphenyl)1,3,5-triazine;

2-(2',4'-dimethylphenyl)-4,6-bis(2'-hydroxy-4'-n-octyloxyphenyl)-1,3,5-triazine;

2-phenyl-4,6-bis(2'-hydroxy-4'-n-octyloxyphenyl)-1,3,5-triazine;

2-phenyl-4,6-bis(2'-hydroxy-4'-n-octyloxyphenyl)-1,3,5-triazine;

2-phenyl-4-{[4-(3-(2-propyloxy)-2-hydroxypropyloxy)-2-hydroxy]phenyl}-6-(4-methoxyphenyl)-1,3,5-triazine;

2-(4'-methylphenyl)-4,6-bis{[4-(2-ethylhexyloxy)-2-hydroxy]phenyl}-1,3,5-triazine;

2-(2',4'-dimethylphenyl)-4,6-bis{[4-(2-ethylhexyloxy)-2-hydroxy]phenyl}-1,3,5-triazine;

2-phenyl-4,6-bis{[4-(2-ethylhexyloxy)-2-hydroxy]lphenyl}-1,3,5-triazine;

2-phenyl-4,6-bis{[4-(tris(trimethysiloxysilylpropyloxy)-2-hydroxy]phenyl}-1,3,5-triazine;

2-phenyl-4,6-bis{[4-(2"methylpropenyloxy)-2-hydroxy]phenyl}-1,3,5-triazine;

2-phenyl-4,6-bis{[4-(3(2-propyloxy)-2-hydroxypropyloxy)-2-hydroxy]phenyl}-1,3,5-triazine; or 2-phenyl,4,6-bis{[4-(2-ethylhexyloxy)-2-hydroxy]phenyl}-1,3,5-triazine.

Other examples of triazine derivatives are listed in Table 1:

TABLE 1

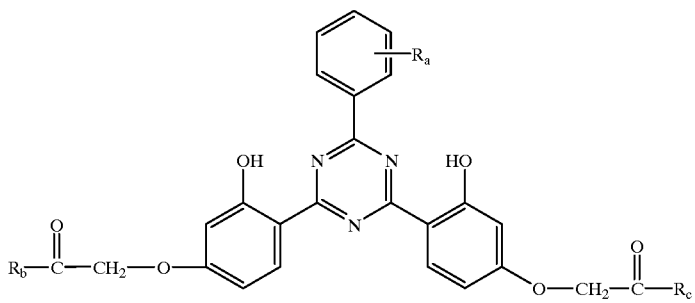

| $R_a$ | $R_b$ | $R_c$ |
|---|---|---|
| H | H₃C—C(CH₃)₂—O— | H₃C—C(CH₃)₂—O— |
| CH₃ | H₃C—C(CH₃)₂—O— | H₃C—C(CH₃)₂—O— |
| H | —NH—C₆H₄—COOC₄H₉ | —NH—C₆H₄—COOC₄H₉ |
| CH₃ | —NH—C₆H₄—COOC₄H₉ | —NH—C₆H₄—COOC₄H₉ |
| H | —OH | —OH |
| CH₃ | —OH | —OH |
| H | —OH | —OH |
| H | —OM<br>M = alkali metal, alkaline earth metal, Cu, Zn, Mg | —OM<br>M = alkali metal, alkaline earth metal, Cu, Zn, Mg |
| CH₃ | —OM<br>M = alkali metal, alkaline earth metal, Cu, Zn, Mg | —OM<br>M = alkali metal, alkaline earth metal, Cu, Zn, Mg |
| H | O⁻⁺N(CH₂CH₂OH)₃ | O⁻⁺N(CH₂CH₂OH)₃ |
| CH₃ | O⁻⁺N(CH₂CH₂OH)₃ | O⁻⁺N(CH₂CH₂OH)₃ |
| H | H₃C—N⁺(CH₃)₂—(CH₂)ₙ—O—<br>n = 2–14 | H₃C—N⁺(CH₃)₂—(CH₂)ₙ—O—<br>n = 2–14 |
| CH₃ | H₃C—N⁺(CH₃)₂—(CH₂)ₙ—O—<br>n = 2–14 | H₃C—N⁺(CH₃)₂—(CH₂)ₙ—O—<br>n = 2–14 |
| H | HOCH₂CH(OH)CH₂CH₃ | HOCH₂CH(OH)CH₂CH₃ |
| CH₃ | HOCH₂CH(OH)CH₂CH₃ | HOCH₂CH(OH)CH₂CH₃ |

TABLE 1-continued

| $R_a$ | $R_b$ | $R_c$ |
|---|---|---|
| H | (retinyl-type group: trimethylcyclohexenyl-polyene-OMe) | (retinyl-type group: trimethylcyclohexenyl-polyene-OMe) |
| CH$_3$ | (retinyl-type group) | (retinyl-type group) |
| H | (tocopheryl-type group) | (tocopheryl-type group) |
| CH$_3$ | (tocopheryl-type group) | (tocopheryl-type group) |
| H | (aminosugar group) | (aminosugar group) |
| CH$_3$ | (aminosugar group) | (aminosugar group) |

The bis(resorcinyl)triazines which may be used in accordance with this invention can be prepared in different manner, for example using aromatic nitrite compounds as starting compounds. The dichlorotriazine compound of formula

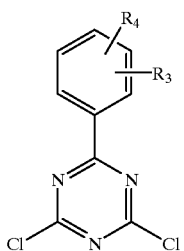

(1k)

can be prepafor example, by reacting benzonitrile with dicyandiamide to the diaminotriazine compound which is subsequently saponified to the dihydroxytriazine (tautomer=dione) and then converted to the dichlorotriazine compound of formula (1k) with thionyl chloride. The two resorcinol groups are then introduced in commonly known manner by Friedel-Crafts acylation of resorcinol in the presence of a Lewis acid, preferably aluminium chloride. In the third step, the free hydroxyl groups in p-position are etherified, depending on the meaning of $R_1$ and $R_2$ in the compound of formula (1) by alkylation or acid-catalysed addition of glycidyl ethers.

Other processes for the preparation of the triazine derivatives which can be used in accordance with this invention are descnbed in EP-A-0,775,698.

The bis(resorcinyl)triazine compounds of formula (1) used according to this invention are particularly suitable as UV filters, i.e. for protecting ultraviolet-sensitive organic materials, in particular human and animal skin and hair, from the harmful effect of UV radiation. These compounds are, in particular, very powerful UVA absorbers with fractions in the UVB range and can be produced at low cost Accordingly, these compounds are suitable for use as light stabilisers in cosmetic, pharmaceutical and veterinary compositions. They can be used in dissolved as well as in micronised state.

Accordingly, this invention also relates to a cosmetic formulation, which comprises at least one compound of formula (1) as well as cosmetically compatible carriers or auxiliaries.

For cosmetic use, the light stabilisers of this invention usually have an average particle size in the range from 0.02 to 2, preferably from 0.05 to 1.5 and, most preferably, from 0.1 to 1.0 m. The insoluble UV absorbers used according to this invention can be brought to the desired particle size by customary methods, for example by grinding e.g. with a jet, ball, vibratory or hammer mill. Grinding is preferably carried out in the presence of 0.1 to 30 by weight, preferably of 0.5 to 15% by weight, based on the UV absorber, of a grinding aid such as an alkylated vinylpyrrolidone polymer, vinylpyrrolidonevinylacetate copolymer, acylglutamate or, preferably, phospholipid.

In addition to the inventive UV absorbers, the cosmetic formulation can also contain one or more than one other UV protective, for example an organic UV absorber from the classes of the p-aminobenzoic acid derivatives, salicylic acid derivatives, benzophenone derivatives, dibenzoylmethane derivatives, diphenylacrylate derivatives, benzofuran derivatives, polymeric UV absorbers comprising one or more than one organosilicon radical, cinnamic acid derivatives, camphor derivatives, trianilino-s-triazine derivatives, phenylbenzimidazolesuffonic acid and the salts thereof, menthylanthranilates, benzotriazole derivatives, and/or an inorganic micropigment selected from the group consisting of aluminium oxide- or silicium dioxide-coated $TiO_2$, zinc oxide or mica.

Examples of p-aminobenzoic acid derivative compounds:

4-aminobenzoic acid (PABA); ethyldihydroxypropyl-PABA of formula (4)

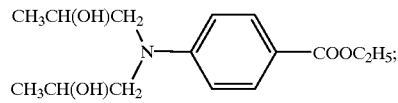

PEG-25-PABA of formula (5)

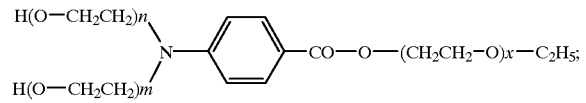

wherein m, n and x have the same meaning and are each at most 25;

octyidimethyl PABA of formula (6)

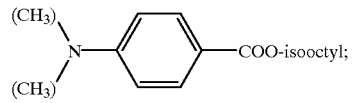

or glycylaminobenzoate of formula (7)

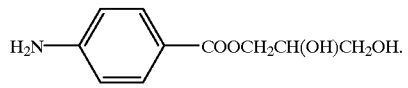

Examples of salicylic acid derivative compounds:
homomenthylsalicylate of formula (8)

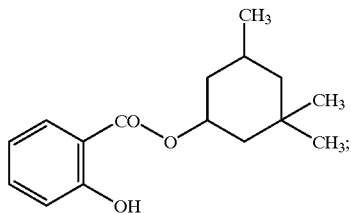

triethnanolaminosalicyiate of formula (9)

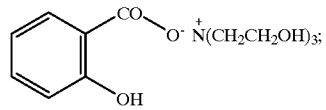

amyl-p-dimethylaminobenzoate of formula (10)

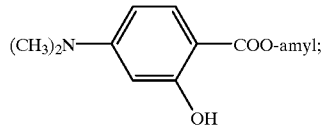

octylsalicylate of formula (11)

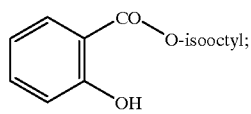

or 4-isopropylbenzyl-salicylate of formula (12)

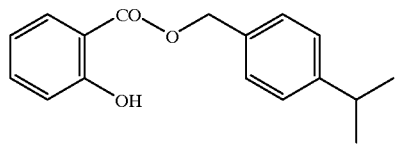

Examples of benzophenone derivative compounds:
benzophenone-3-(2-hydroxy-4-methoxybenzophenone), benzophenone-4-(2-hydroxy-4-methoxybenzophenone-5-sulfonic acid) or benzophenone-8-(2,2'-dihydroxy-4-methoxybenzophenone).
Examples of dibenzoylmethane derivative compounds:
butylmethoxydibenzoylmethane[1-(4-tert-butyl)-3-(4-methoxyphenyl) propane-1,3-dione].
Examples of diphenylacrylate derivative compounds:
octocrylene(2-ethylhexyl-2-cyano3,3'-diphenyacrylate) or etocrylene (ethyl-2-cyano-3,3'-diphenylacrylate).
Examples of benzofuran derivative compounds:
3-(benzofuranyl)-2-cyanoacrylate, 2-(2-benzofuranyl)-5-tert-butylbenzoxazole or 2-(p-aminophenyl) benzofurane and, in particular, the compound of formula (13)

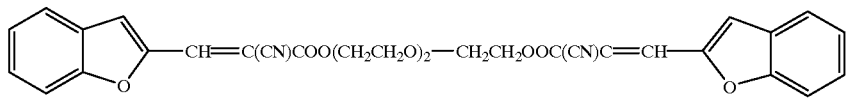

or

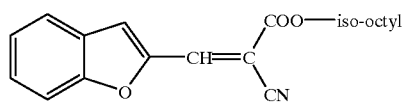

(14)

benzylidenemalonate derivative, in particular the compound of formula (15)

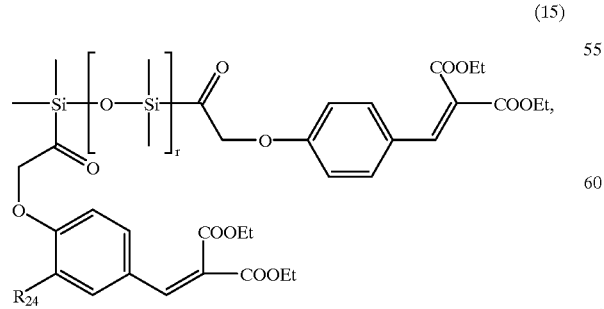

wherein $R_{24}$ is hydrogen or O-Me and
r is approximately 7; the compound of formula (16)

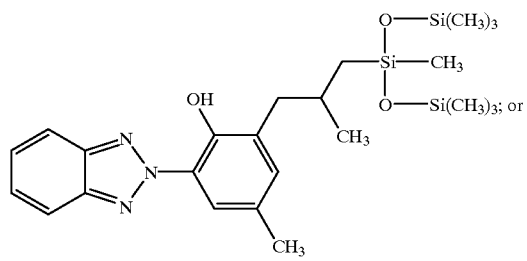

(17)

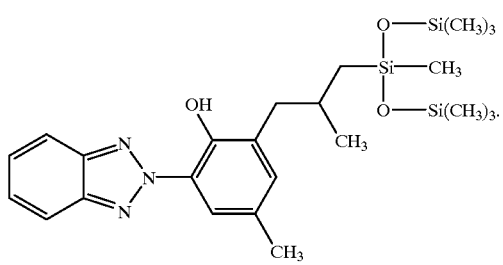

Examples of cinnamate compounds:
octylmethoxycinnamate (4-methoxycinnamic acid-2-ethylhexy, diethanolaminometho-xycinnamate (the diethanolamine salt of 4-methoxycinnamic acid), isoamyl-p-methoxy-cinnamate (4-ethoxycinnamic acid-2-isoamyl), 2,5-diisopropylmethylcinnamate or a cinnamic acid amido derivative.

Examples of camphor derivative compounds:
4-methyl-benzylidenecamphor [3-(4'-methyl) benzylideneboman-2-one], 3-benzylidene-camphor (3-benzylidenebornan2-one), polyacrylamidomethyl-benzylidenecamphor {N-[2(and 4)-2-oxybom-3-ylidenemethyl)benzyl]acrylamide polymer}, trimoniumbenzylidenecamphorsulfate-[3-(4'-trimethylammonium) benzylidenebornan-2-onemethylsul-fate], terephthalydenedicamphorsulfonic acid {3,3'-(1,4-phenylenedimethine)-bis (7,7-dimethyl-2-oxobicydo-[2.2.1]heptane-1-methanesulfonic acid} or the salts thereof, or benzylidenecamphorsulfonic acid [3-(4'-sulfo)benzylidenebornan-2-one] or the salts thereof.
Examples of trianilino-s-triazine derivative compounds:
octyltriazine-[2,4,6-trianilino-(p-carbo-2'-ethyl-1'-oxy)-1,3,5-triazine, and also the trianilino-s-triazine derivatives disclosed in U.S. Pat. Nos. 5,332,568, 5,252,323, WO 93/117002 and WO 97/03642 and EP-A-0,517, 104.

Examples of benzotriazole compounds:
2-(2-hydroxy-5-methylphenyl)benzotriazole.

The novel cosmetic formulation comprises 0.1 to 15 by weight, preferably 0.5 to 10% by weight, based on the total weight of the formulation, of a UV absorber or of a mixture of UV absorbers as well as a cosmetcally compatible auxiliary.

The cosmetic formulation can be prepared by physically mixing the UV absorber(s) with the auxiliary by customary methods, for example by simply stirring the individual components together.

The novel cosmetic formulation can be formulated as water-in-oil or oil-in-water emulsion, as oil-in-alcohol lotion, as vesicular dispersion of a ionic or nonionic amphiphilic lipid, as gel, solid stick or as aerosol formulation.

As water-in-oil or oil-in-water emulsion, the cosmetically compatible auxiliary preferably comprises 5 to 50% of an oil phase, 5 to 20% of an emulsifier and 30 to 90% of water. The oil phase can contain any oil suitable for cosmetic formulations, for example one or more than one hydrocarbon oil, wax, natural oil, silicone oil, fatty acid ester or fatty alcohol. Preferred mono- or polyols are ethanol, isopropanol, propylene glycol, hexylene glycol, glycerol and sorbitol.

It is possible to use any conventional emulsifier for the inventive cosmetic formulation, for example one or more than one ethoxylated ester of natural derivatives, such as polyethoxylated ester of hydrogenated castor oil; or a silicone oil emulsifier.such as silicone polyol; an optionally ethoxylated fatty acid soap; an ethoxylated fatty alcohol; an optionally ethoxylated sorbitan ester; an ethoxylated fatty acid; or an ethoxylated glyceride.

The cosmetic formulation can also contain other components, for example emollients, emulsion stabilisers, skin moisturisers, suntan accelerators, thickeners such as xanthane, moisture retention agents such as glycerol, preservatives, fragrances and colourants.

The novel cosmetic formulation is distinguished by excellently protecting the human skin against the harmful effect of sunlight.

In the following Examples percentages are by weight. The amounts given for the bis(resorcinyl)triazine compounds refer to the pure substance.

EXAMPLES

Use Examples for Cosmetic Light Protection

The light stabilisers are determined in accordance with the method of Diffey and Robson, J. Soc. Cosmet. Chem. 40, 127–133 (1989) using an SPF analyser (Optometrix, SPF 290).

To determine the photostabilities, the filter substances are dissolved in ethanol (c=$1 \cdot 10^{-5}$–$5 \cdot 10^{-5}$ M) and irradiated, with stirring, in a quartz cuvette using a metal halide lamp (Macam) ($I_{UVB}$=0.4–8.0 mW/cm$^2$). To convert to the solar spectrum (CIE D65-norm daylight, standardised to $I_{UVB}$= 0.127 mW/cm$^2$), the integral over the products of the wave-length-resolved lamp intensity and the corresponding absorption values of the respective UV absorbers from 290 to 400 nm is calculated and is then divided by the integral over the products of the D65 light intensities and the corresponding absorption values of the respective UV absorber in the range from 290 to 400 nm. This factor is multiplied with the half life period for degradation under metal halide lamp irradiation to obtain the corresponding half life period under solar irradiation. The half life period for the photodegradation under lamp irradiation is determined via UV-spectroscopic measurement of the extinction at the wavelength of the maximum absorption and subsequent exponential fit. Using the process described, the half life periods for the photodegradation in D65 light are thus obtained.

Example 1 o/w Emulsion with the Compound of Formula (101)

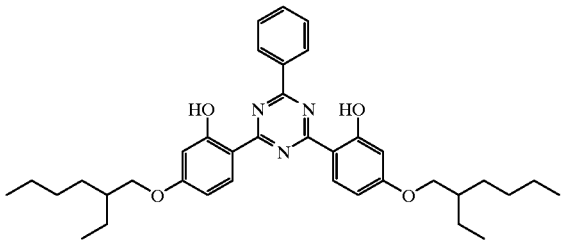

$\lambda_{max}$: 356 nm (ethanol)
$\epsilon_{max}$: 41 400 M$^{-1}$cm$^{-1}$

| (A): | |
|---|---|
| triazine UV absorber of formula (101) | 4 g |
| sesame oil | 10 g |
| glyceryl stearate | 4 g |
| stearic acid | 1 g |
| cetyl alcohol | 0.5 g |
| Polysorbate 20 | 0.2 g |
| (B): | |
| propylene glycol | 4 g |
| propylparaben | 0.05 g |
| methylparaben | 0.15 |
| triethanolamine | 0.1 g |
| Carbomer 934 | 0.1 g |
| water | ad 100 ml |

Preparation of the Emulsion

Phase (A):

The UV absorber is first dissolved in sesame oil and the other components of (A) are then added and fused together.

Phase (B):

Propylparaben and methylparaben are dissolved in propylene glycol. 60 ml water are then added, the mixture is heated to 70° C. and Carbomer 934 is emulsified therein.

Emulsion:

(A) is slowly added to B with vigorous mechanical energy input. The volume is adjusted to 100 ml by addition of water.

The sunscreen factors and photostabilities obtained are compiled in Table 1.

TABLE 1

| | Concentration | Sunscreen factor*) | Photostability**) [h] |
|---|---|---|---|
| compound of formula (101) | 4% | 7.1 | 6000 |

*)according to Diffey and Robson
**)as half life period of the photodegradation in D65 tight in ethanolic solution The sunscreen factor can be varied via the UV absorber concentration.

The results demonstrate that the active substance has high photostability and that a good sunscreen factor may be achieved even at low concentration.

Other physically defined measures for UVA characterisation:

TABLE 2

Other physically defined measures for UVA characterisation

| | compound of formula (101) 4% emulsion |
|---|---|
| T(360)[1] | 0.6% |
| UVA/UVB ratio[2] | 0.79 |
| $\lambda_{crit}$ [nm][3] | 373 |

Example 2

Sunscreen Emulsion Containing New Oil Soluble Filter (101) and Octyl Methoxycinnamate

| Phase | Component | % b.w. |
|---|---|---|
| (A) | Water (aqua), deionized | 54.90 |
| | Xanthan gum, 2% solution | 15.00 |
| | Propylene glycol | 1.50 |
| | Tetrasodium EDTA | 0.10 |
| (B) | Isopropylmyristate | 10.00 |
| | Triazine UV-absorber with formula (101) | 3.00 |
| (C) | Octyl methoxycinnamate | 7.50 |
| | Glyceryl stearate (and) PEG-100 stearate | 3.00 |
| | Cyclomethicone | 1.00 |
| | Cetearyl alcohol (and) ceteareth-20 (Amerchol) | 3.00 |
| (D) | Propylene glycol (and) methylparaben (and) propylparaben (and) diazolidinyl urea (ISP) | 1.00 |

Procedure: The components of (A) are mixed in order and heated to 75° C. Components of (B) are mixed, heated to 75° C. and stirred until filter is dissolved. Then (C) is added to B and mixed for 20 minutes (=mixture (BC)). (D) is then added to (BC) (=mixture (BCD)). (A) is added to (BCD) while mixing and cooling to room temperature.

Resulting SPF (Sun Protection Factor): 16 (method according example 1)

Example 3

Sunscreen Formulation Containing New Water Soluble Filter of the Formula (102) and Octyl Methoxycinnamate

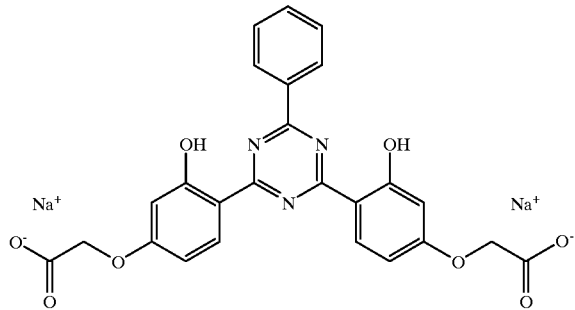

(102)

$I_{max}$=352 nm (ethanol)

$e_{max}$=39 800 $M^{-1}$ $cm^{-1}$

| Phase | Component | % b.w. |
|---|---|---|
| (A) | Triazine UV-absorber with formula (102) | 4.00 |
| | Carbomer | 0.30 |
| (B) | water (aqua), deionized | 57.93 |
| (C) | Propylene glycol | 5.00 |
| | Methylparaben | 0.20 |
| | Propylparaben | 0.10 |
| | Triethanolamine | 0.45 |
| | Tetrasodium EDTA | 0.02 |
| (D) | Octyl methoxycinnamate | 5.00 |
| | Glyceryl stearate (and) PEG-100 stearate | 1.00 |
| | Cyclomethicone | 5.00 |
| | Glyceryl stearate | 4.00 |
| | Stearic acid | 2.50 |
| | Isostearyl isostearate | 10.00 |
| | Hydrogenated castor oil | 2.00 |
| | $C_{12-15}$ alkyl benzoate | 2.50 |

Procedure: (A) is dispersed in (B) and, when uniform, components of (C) (=mixture (ABC)) are added in order. While heating to 85° C., components of (D) are combined in a separate vessel and heated with mixing to 85° C. When (ABC) and (D) are both at 85° C. and uniform, (D) is slowly added to ABC with strong mixing. 15 minutes after the last of D has been added cooling batch is started and cool to room temperature.

Resulting SPF (Sun Protection Factor): 12 (method according example 1)

What is claimed is:

1. A method of protecting human and animal skin and hair from the damaging effect of UV radiation which comprises applying to said human or animal skin or hair a UV absorber of formula

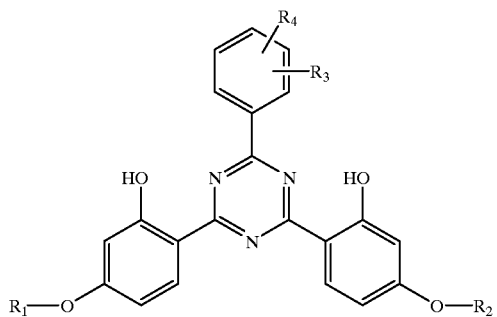
(1)

wherein $R_1$ and $R_2$ are each independently of the other hydrogen; branched $C_5$–$C_{18}$alkyl; $C_2$–$C_{18}$alkenyl; a radical of formula —$CH_2$—$CH$(—OH)—$CH_2$—O—$T_1$; a radical of formula (1a)

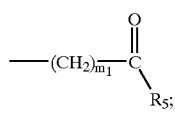
(1a)

or a radical of formula (1b)

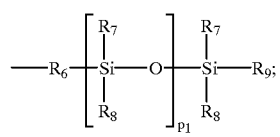
(1b)

$R_3$ and $R_4$ are each independently of the other hydrogen or $C_1$–$C_5$alkyl;

$R_5$ is hydroxy; $C_1$–$C_5$alkoxy which is unsubstituted or substituted by one or several OH groups; amino; mono- or di-$C_1$–$C_5$alkylamino; M; a radical of formula

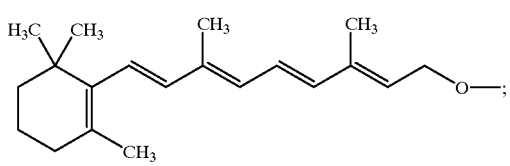
(1c)

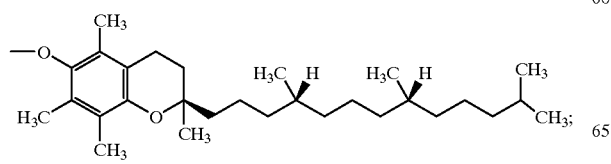
(1d)

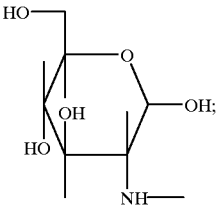
(1e)

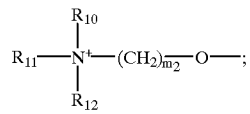
(1f)

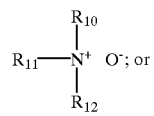
(1g)

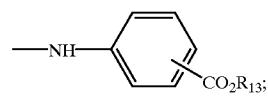
(1h)

$R_6$ is a direct bond; a straight-chain or branched $C_1$–$C_4$alkylene radical or a radical of formula

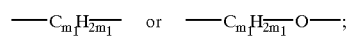

—$C_{m_1}H_{2m_1}$—  or  —$C_{m_1}H_{2m_1}$O—;

$R_7$, $R_8$ and $R_9$ are each independently of one another $C_1$–$C_{18}$alkyl; $C_1$–$C_{18}$alkoxy or a radical of formula

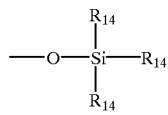
(1i)

$R_{10}$, $R_{11}$ and $R_{12}$ are each independently of one another $C_1$–$C_{14}$alkyl which is unsubstituted or substituted by one or several OH groups;

$R_{13}$ is hydrogen; M; $C_1$–$C_5$alkyl; or a radical of formula —$(CH_2)_{m_2}$—O—$T_1$;

$R_{14}$ is $C_1$–$C_5$alkyl;

M is a metal cation;

$T_1$ is hydrogen; or $C_1$–$C_8$alkyl;

$m_1$ is 1 to 3;

$m_2$ is 2 to 14; and $p_1$ is 0; or a number from 1 to 5.

2. A method according to claim 1, wherein the bis (resorcinyl)triazine used is the compound of formula (2)

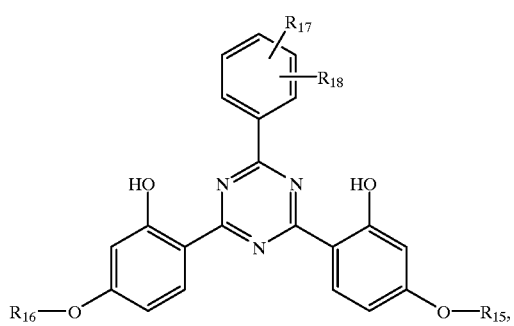

wherein
- $R_{15}$ and $R_{16}$ are each independently of the other branched $C_5$–$C_{18}$alkyl or —$CH_2$—$CH(—OH)$—$CH_2$-O—$T_1$;
- $R_{17}$ and $R_{18}$ are hydrogen; and
- $T_1$ is hydrogen; or $C_1$–$C_5$alkyl.

3. A method according to claim 2, wherein, in formula (2), $R_{15}$ and $R_{16}$ are each independently of the other $C_1$–$C_{18}$alkyl or —$CH_2$—$CH(—OH)$—$CH_2$—$O$—$T_1$; $R_{17}$ and $R_{18}$ are hydrogen; and $T_1$ is hydrogen; or $C_1$–$C_5$alkyl.

4. A method according to claim 3, wherein, in formula (2), $R_{15}$ and $R_{16}$ are each independently of the other branched $C_{5-18}$alkyl; and $R_{17}$ and $R_{18}$ are hydrogen.

5. Use according to claim 2, wherein R and $R^{16}$ in formula (2) have the same meaning.

6. A method according to claim 1, which comprises using a bis(resorcinyl)triazine of formula (3)

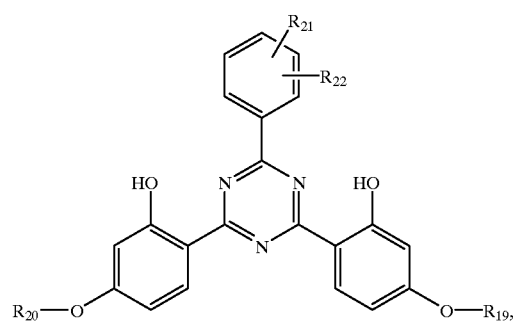

wherein
- $R_{19}$ and $R_{20}$ are each independently of the other the radical of formula

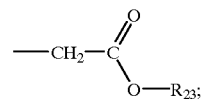

and $R_{21}$, $R_{22}$ and $R_{23}$ are each independently of one another hydrogen; or $C_1$–$C_{10}$alkyl.

7. A cosmetic formulation, which comprises a UV absorber of formula (1) as defined in claim 1 together with a cosmetically compatible carrier or auxiliary.

8. A formulation according to claim 7, which comprises an additional UV protective agent.

9. A formulation according to claim 8, wherein the additional UV protective agent is
- an organic UV absorber selected from the group consisting of p-aminobenzoic acid derivatives, salicylic acid derivatives, benzophenone derivatives, dibenzoyimethane derivatives, diphenylacrylate derivatives, benzofuran derivatives, polymeric UV absorbers comprising one or more than one organosilicon radical, cinnamic acid derivatives, camphor derivatives, trianilino-s-triazine derivatives, phenylbenzimidazolesulfonic acid and the salts thereof, menthylanthranilates, benzotriazole derivatives;
- an inorganic micropigment selected from the group consisting of aluminium oxide- or silicon dioxide-coated $TiO_2$, zinc oxide or mica, or
- a mixture of said additional UV protective agents.

10. A method according to claim 1, wherein the UV absorber of formula (1) comprises 0.1 to 15% by weight of a cosmetic composition.

11. A method according to claim 1, wherein the UV absorber is of formula (101)

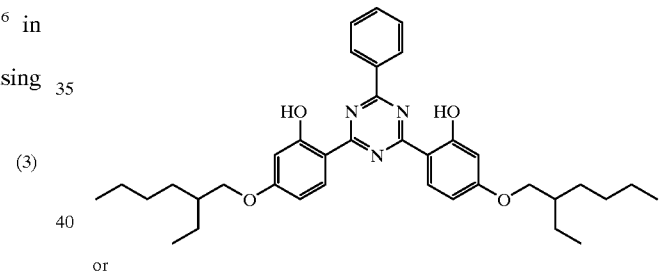

or (102)

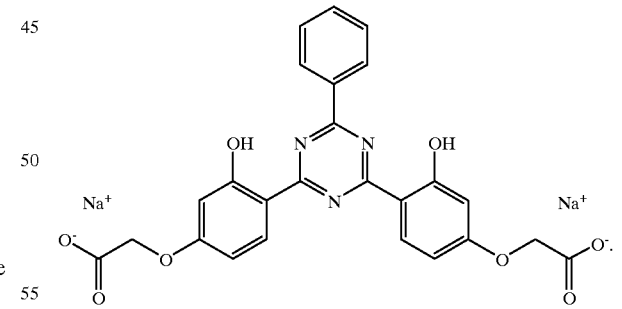

12. A cosmetic formulation according to claim 7, which is an water-in-oil or oil-in-water emulsion, an oil-in-alcohol lotion, a vesicular dispersion of a ionic or nonionic amphiphilic lipid, a gel, solid stick or aerosol formulation.

* * * * *